(12) United States Patent
Nagae et al.

(10) Patent No.: US 10,485,500 B2
(45) Date of Patent: Nov. 26, 2019

(54) X-RAY DIAGNOSTIC APPARATUS

(71) Applicant: Toshiba Medical Systems Corporation, Otawara (JP)

(72) Inventors: Ryoichi Nagae, Nasushiobara (JP);
Yasuto Hayatsu, Otawara (JP);
Yoshiaki Iijima, Nasushiobara (JP);
Takuya Sakaguchi, Utsunomiya (JP);
Yuichiro Watanabe, Yaita (JP)

(73) Assignee: Canon Medical Systems Corporation, Otawara-shi (JP)

( * ) Notice: Subject to any disclaimer, the term of this patent is extended or adjusted under 35 U.S.C. 154(b) by 280 days.

(21) Appl. No.: 15/481,066

(22) Filed: Apr. 6, 2017

(65) Prior Publication Data

US 2017/0290556 A1    Oct. 12, 2017

(30) Foreign Application Priority Data

Apr. 6, 2016 (JP) ................................. 2016-076506

(51) Int. Cl.
*A61B 6/02* (2006.01)
*A61B 6/00* (2006.01)

(52) U.S. Cl.
CPC .............. *A61B 6/466* (2013.01); *A61B 6/469* (2013.01); *A61B 6/5235* (2013.01)

(58) Field of Classification Search
CPC ........... A61B 6/00; A61B 6/466; A61B 6/469; A61B 6/5235; A61B 6/02; A61B 6/022; A61B 6/481; A61B 6/54; A61B 6/541; A61B 6/542; A61B 6/503; A61B 6/504; A61B 6/5217; A61B 6/461; A61B 6/463
USPC .............................. 378/41, 62, 95, 98.2, 98.5
See application file for complete search history.

(56) References Cited

U.S. PATENT DOCUMENTS

| 7,180,976 B2 | 2/2007 | Wink et al. |
| 7,203,534 B2 | 4/2007 | Mollus et al. |
| 2014/0035914 A1* | 2/2014 | Noshi .................... G06T 15/08 345/424 |
| 2014/0198897 A1 | 7/2014 | Sakaguchi et al. |
| 2014/0205061 A1 | 7/2014 | Sakaguchi et al. |

FOREIGN PATENT DOCUMENTS

| JP | 2003-245273 | 9/2003 |
| JP | 2005-528157 | 9/2005 |
| JP | 5121173 | 1/2013 |
| JP | 2013-81690 | 5/2013 |
| JP | 2013-233317 | 11/2013 |
| JP | 2013-233319 | 11/2013 |
| JP | 5500931 | 5/2014 |

* cited by examiner

*Primary Examiner* — Jurie Yun
(74) *Attorney, Agent, or Firm* — Oblon, McClelland, Maier & Neustadt, L.L.P.

(57) ABSTRACT

An X-ray diagnostic apparatus of an embodiment includes processing circuitry. The processing circuitry acquires two medical images, a moving distance of a region of interest between the medical images corresponding to a distance derived from a parallax angle. The processing circuitry causes a display to display a stereoscopic image based on the medical images.

10 Claims, 12 Drawing Sheets

<FRAME GROUP>

<LEFT EYE IMAGE>

<FRAME GROUP>

<RIGHT EYE IMAGE>

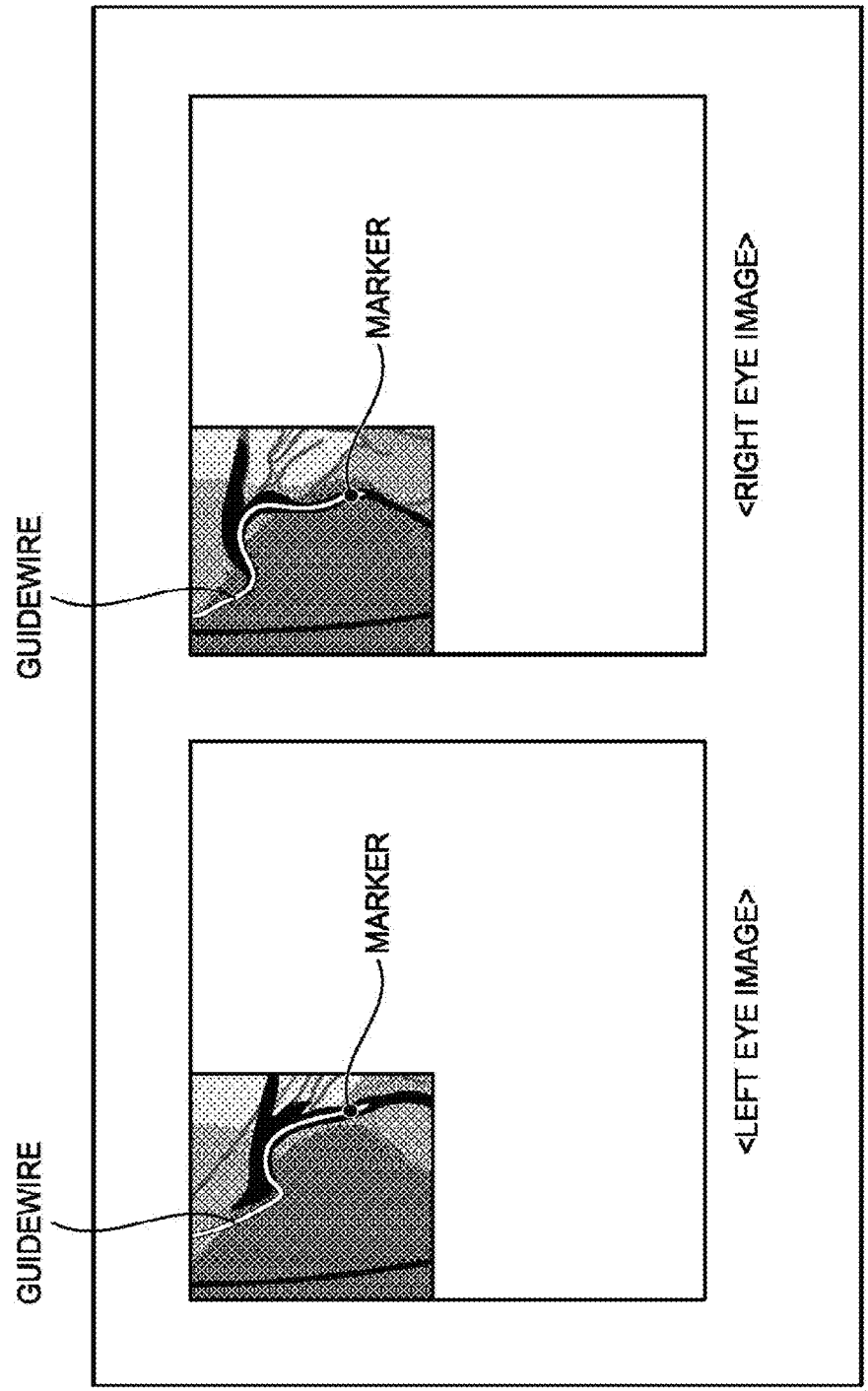

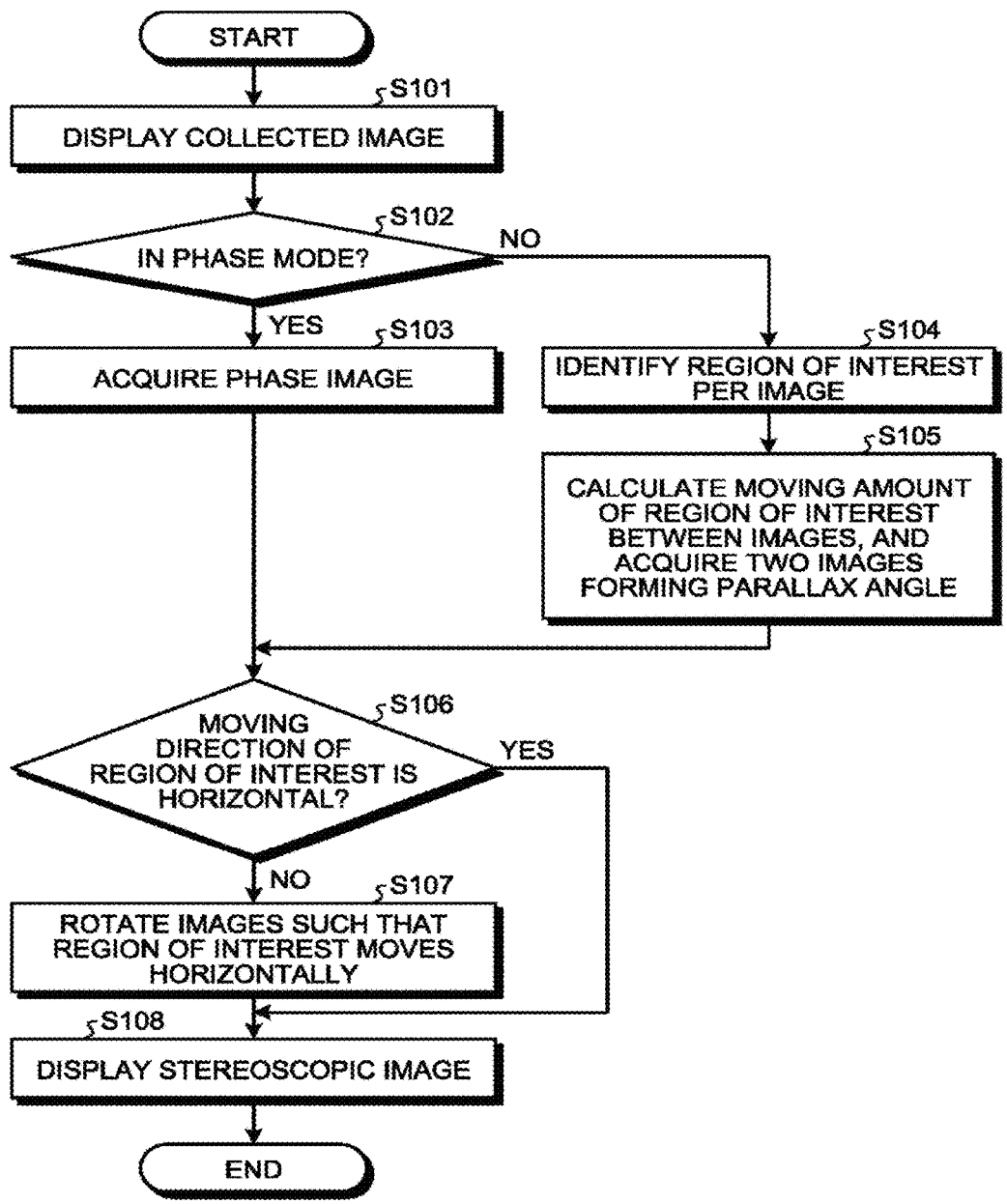

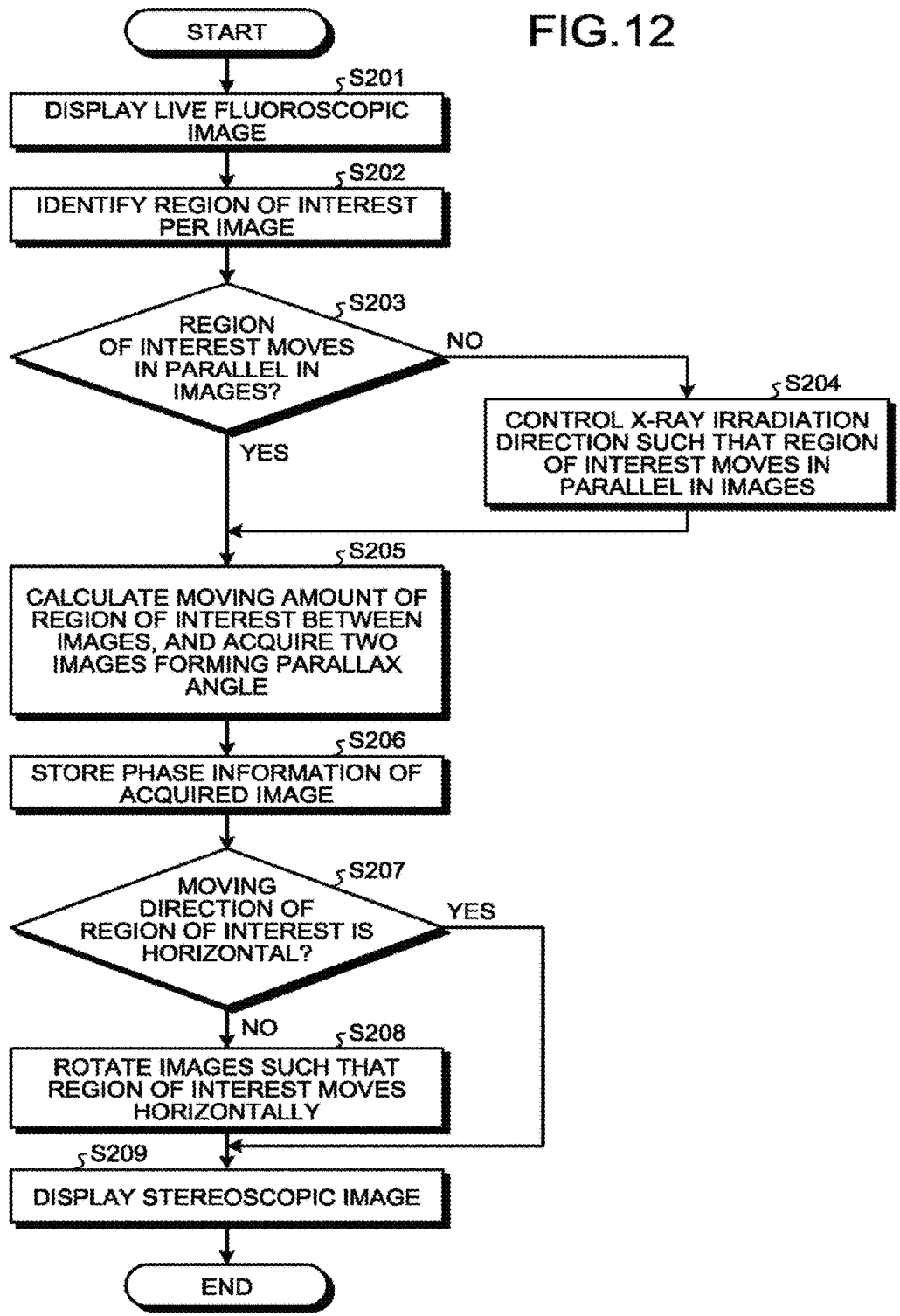

X-RAY DIAGNOSTIC APPARATUS

CROSS-REFERENCE TO RELATED APPLICATIONS

This application is based upon and claims the benefit of priority from Japanese Patent Application No. 2016-076506, filed on Apr. 6, 2016; the entire contents of which are incorporated herein by reference.

FIELD

Embodiments described herein relate generally to an X-ray diagnostic apparatus.

BACKGROUND

Conventionally, a technique of having a stereoscopic view of a medical image by using a three-dimensional (3D) monitor has been known. For example, a 3D monitor enabling to have a stereoscopic view from parallax images that are imaged from two view points by using a special device such as stereoscopic glasses has been in actual use. Moreover, for example, a 3D monitor enabling to have a stereoscopic view without glasses from multiple parallax images (for example, parallax images from two points, parallax images from nine points, and the like) by using a beam controller such as a lenticular lens has been in actual use. By displaying a medical image on such a 3D monitor, an observer can obtain information in a direction of depth, and can understand spatial positional relationship easily.

BRIEF DESCRIPTION OF THE DRAWINGS

FIG. 10A shows a display example of parallax images by the control function according to the first embodiment;
FIG. 11 is a flowchart showing a processing procedure of a post process according to the first embodiment;
and
FIG. 12 is a flowchart showing a processing procedure at the time of Live according to the first embodiment.

DETAILED DESCRIPTION

According to an embodiment, an X-ray diagnostic apparatus includes processing circuitry. The processing circuitry is configured to acquire two medical images, a moving distance of a region of interest between the medical images corresponding to a distance derived from a parallax angle. The processing circuitry is configured to cause a display to display a stereoscopic image based on the medical images.

Embodiments of an X-ray diagnostic apparatus according to the present application are explained in detail below with reference to the accompanying drawings. The X-ray diagnostic apparatus according to the present application is not limited by the embodiments below.

First Embodiment

Figure 1:
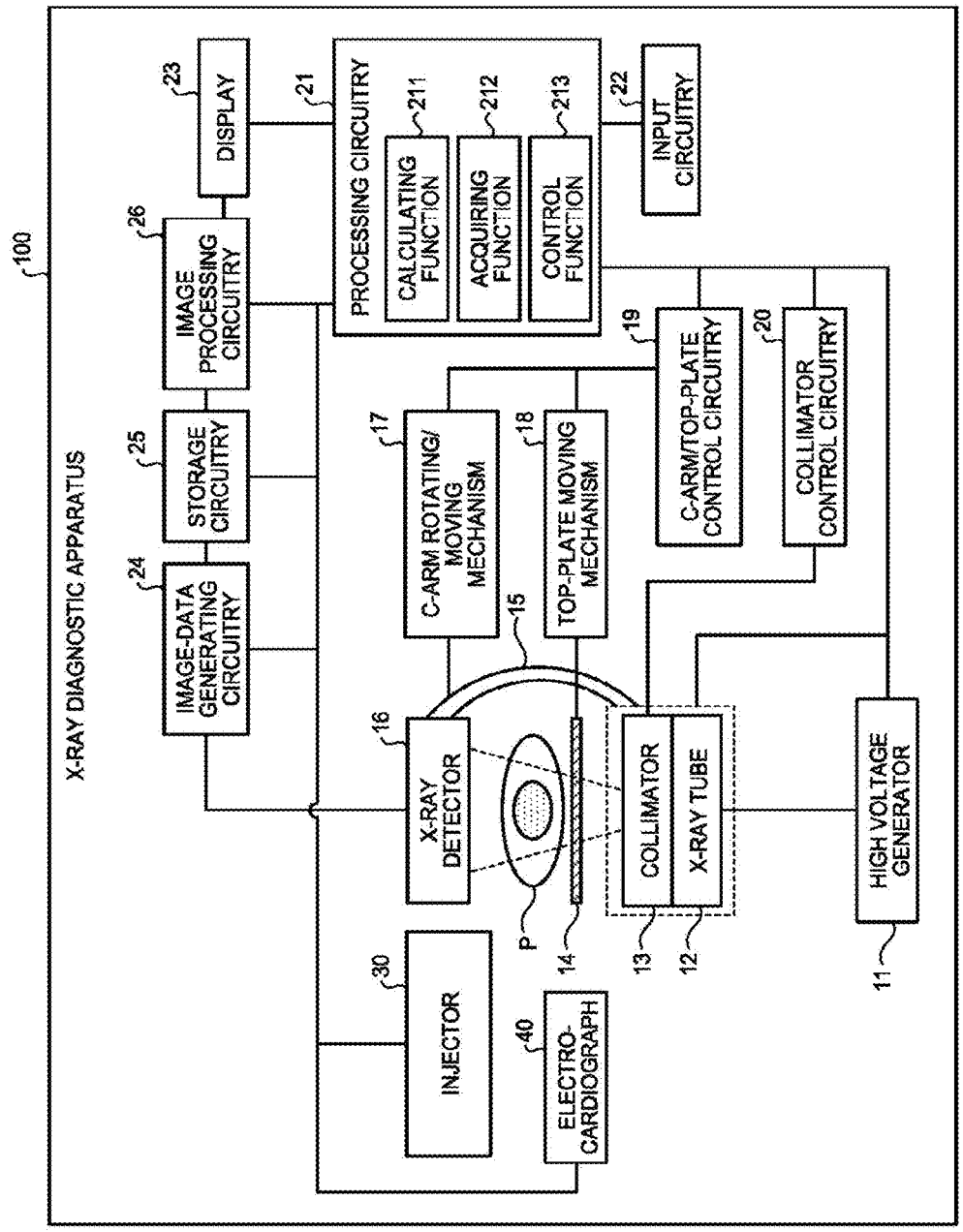
FIG. 1 shows one example of a configuration of an X-ray diagnostic apparatus according to a first embodiment.

FIG. 1 shows one example of a configuration of an X-ray diagnostic apparatus 100 according to a first embodiment. As shown in FIG. 1, the X-ray diagnostic apparatus 100 according to the first embodiment includes a high voltage generator 11, an X-ray tube 12, a collimator 13, a top plate 14, a C arm 15, and an X-ray detector 16. Furthermore, the X-ray diagnostic apparatus 100 according to the first embodiment includes a C-arm rotating/moving mechanism 17, a top-plate moving mechanism 18, C-arm/top-plate control circuitry 19, collimator control circuitry 20, processing circuitry 21, input circuitry 22, and a display 23. Moreover, the X-ray diagnostic apparatus 100 according to the first embodiment includes image-data generating circuitry 24, storage circuitry 25, and image processing circuitry 26. Furthermore, the X-ray diagnostic apparatus 100 is connected to an injector 30 and an electrocardiograph 40. In the X-ray diagnostic apparatus 100, the respective circuits are connected to each other, as shown in FIG. 1, and communicate various kinds of electrical signals among the circuits, or communicate an electrical signal with the injector 30.

The injector 30 is a device to inject a contrast agent through a catheter inserted in a subject P. The injection of a contrast agent from the injector 30 is performed according to an injection instruction that is received through the processing circuitry 21 described later. Specifically, the injector 30 performs contrast agent injection according to contrast-agent injection conditions including an injection start instruction, an injection stop instruction, an injection speed and the like of a contrast agent received from the processing circuitry 21 described later. The injector 30 can also perform injection start and injection stop according to an injection instruction that is directly input to the injector 30 by an operator.

The electrocardiograph 40 acquires an electrocardiogram (ECG) of the subject P to which terminals not shown are attached, and transmits the acquired electrocardiogram to the processing circuitry 21, the image-data generating circuitry 24, and the image processing circuitry 26 together with time information.

In the X-ray diagnostic apparatus 100 shown in FIG. 1, respective processing functions are stored in the storage circuitry 25 in a form of computer-executable programs. The C-arm/top-plate control circuitry 19, the collimator control circuitry 20, the processing circuitry 21, the image-data generating circuitry 24, and the image processing circuitry 26 are processors that implement a function corresponding to each program, by reading and executing a program from the storage circuitry 25. In other words, the respective circuitry that has read the respective programs are to have the function corresponding to the read program.

The term "processor" used in the above explanation signifies, for example, a central processing unit (CPU), a graphical processing unit (GPU), or a circuit, such as an application-specific integrated circuit (ASIC), a simple programmable logic device (SPLD), a complex programmable logic device (CPLD), and a field programmable gate array (FPGA). The processor reads and executes a program stored in the storage circuitry, thereby implementing the function. Instead of storing a program in the storage circuitry, it can be configured to install the program directly in a circuit of a processor. In this case, the processor reads and executes the program installed in a circuit of the processor, thereby implementing the function. The processors of the present embodiment are not limited to be configured as each single circuit per processor, but can be configured as one processor in which multiple independent circuits are combined, thereby implementing the functions.

The high voltage generator 11 generates a high voltage under control of the processing circuitry 21, and supplies the generated high voltage to the X-ray tube 12. The X-ray tube 12 generates an X-ray using the high voltage supplied from the high voltage generator 11.

The collimator 13 narrows an X-ray that has been emitted from the X-ray tube 12 so as to be irradiated selectively to a region of interest of the subject P, under control of the collimator control circuitry 20. For example, the collimator 13 has slidable four collimator blades. The collimator 13 slides the collimator blades to narrow an X-ray that is generated by the X-ray tube 12 under control of the collimator control circuitry 20, to irradiate onto the subject P. The top plate 14 is a bed on which the subject P is laid, and is arranged on a bedstead not shown. Note that the subject P is not included in the X-ray diagnostic apparatus 100.

The X-ray detector 16 detects an X-ray that has passed through the subject P. For example, the X-ray detector 16 has detecting devices that are arranged in matrix. Each detecting device converts an X-ray that has passed through the subject P into an electrical signal and accumulates the signal, and transmits the accumulated signal to the image-data generating circuitry 24.

The C arm 15 holds the X-ray tube 12, the collimator 13, and the X-ray detector 16. The X-ray tube 12 and the collimator 13, and the X-ray detector 16 are arranged so as to oppose to each other having the subject P in between by the C arm 15. Although it is explained with an example in which the X-ray diagnostic apparatus 100 is of a single plane in FIG. 1, embodiments are not limited thereto, and it can be of a biplane.

The C-arm rotating/moving mechanism 17 is a mechanism to rotate and move the C arm 15, and the top-plate moving mechanism 18 is a mechanism to move the top plate 14. The C-arm/top-plate control circuitry 19 adjusts rotation and movement of the C arm 15 and movement of the top plate 14 by controlling the C-arm rotating/moving mechanism 17 and the top-plate moving mechanism 18 under control of the processing circuitry 21. The collimator control circuitry 20 controls an irradiation range of an X-ray to be irradiated on the subject P by adjusting a collimator of the collimator blades included in the collimator 13 under control of the processing circuitry 21.

The image-data generating circuitry 24 generates image data by using the electrical signal that has been converted from an X-ray by the X-ray detector 16, and stores the generated image data in the storage circuitry 25. For example, the image-data generating circuitry 24 subjects the electrical signal received from the X-ray detector 16 to current/voltage conversion, analog (A)/digital (D) conversion, and parallel/serial conversion, to generate image data. A one example, the image-data generating circuitry 24 can generate image data (mash image) that is imaged in a state in which a contrast agent is not injected, and image data (contrast image) that is imaged in a state in which a contrast agent is injected. The image-data generating circuitry 24 stores the generated image data in the storage circuitry 25.

The storage circuitry 25 accepts and stores the image data generated by the image-data generating circuitry 24. Moreover, the storage circuitry 25 stores the programs that are read and executed by the respective circuitry shown in FIG. 1 corresponding to the respective functions. As one example, the storage circuitry 25 stores a program that corresponds to a calculating function 211, a program corresponding to an acquiring function 212, and a program corresponding to a control function 213.

The image processing circuitry 26 generates an X-ray image by performing various kinds of processing on the image data stored in the storage circuitry 25, and stores the image in the storage circuitry 25. For example, the image processing circuitry 26 reads a mask image and a contrast image that are stored in the storage circuitry 25, and performs subtraction (log subtraction) to generate a difference image. The image processing circuitry 26 uses one frame right before injection of a contrast agent as a mask image, and thus, an error in registration due to movement of a body can be minimized. Moreover, the image processing circuitry 26 can perform noise reduction processing by an image processing filter, such as a moving average filter (smoothing), a Gaussian filter, and a median filter. That is, the image processing circuitry 26 can perform preprocessing including position correction and noise reduction for each of a group of multiple pieces of image data that are imaged over time using a contrast agent.

The input circuitry 22 is implemented by a trackball, a switch button, a mouse, a keyboard, and the like to perform settings of a region (for example, a region of interest such as a focused part). The input circuitry 22 is connected to the processing circuitry 21, and converts an input operation received from an operator into an electrical signal to output to the processing circuitry 21.

The display 23 displays a graphical user interface (GUI) to accept an instruction of an operator, and various kinds of images that are generated by the image processing circuitry 26. For example, the display 23 displays an X-ray image that is stored in the storage circuitry 25. The display 23 is a 3D monitor that displays a stereoscopic image that enables an observer to have a stereoscopic view by displaying parallax images that are acquired by the processing circuitry 21 described later. For example, the display 23 displays an image in a three-dimensional manner by a shutter system. As one example, the display 23 displays images for a right eye (hereinafter, right eye images), images for a left eye (hereinafter, left eye images) alternately, for example, at 120 hertz (Hz). The display 23 has an infrared-ray emitting unit, and the infrared-ray emitting unit controls emission of an infrared ray, matching the switching timing between the right eye image and the left eye image.

The observer wears shutter glasses as stereoscopic glasses. The shutter glasses have an infrared-ray receiving unit. The infrared-ray receiving unit receives an infrared ray that is emitted from the infrared-ray emitting unit of the display 23, and switches between a shielding mode and a transmission mode of shutters that are attached on right and left of the shutter glasses, respectively. That is, in the shutter-system three-dimensional display, the shutters of the shutter glasses are controlled such that the right eye image enters a right eye, and a left eye image enters a left eye of the observer. Note that the display 23 is not limited to a 3D monitor of the shutter system, but can also be, for example, of a polarization system or a system enabling to have a stereoscopic view without glasses by using a beam controller such as a lenticular lens (for example, Japanese Laid-open Patent Publication No. 2005-86414, and the like).

The processing circuitry 21 executes the calculating function 211, the acquiring function 212, and the control function 213, thereby controlling overall operation of the X-ray diagnostic apparatus 100. For example, the processing circuitry 21 reads and executes a program that corresponds to the control function 213 to control the entire apparatus from the storage circuitry 25, thereby performing various kinds of processing. For example, the processing circuitry 21 controls the high voltage generator 11 according to an instruction of an operator that is transmitted from the input circuitry 22, and adjusts a voltage to be supplied to the X-ray tube 12, thereby controlling an amount or OF/OFF of an X-ray to be irradiated to the subject P. Moreover, for example, the processing circuitry 21 controls the C-arm/top-plate control circuitry 19 according to an instruction of the operator, and adjusts rotation and movement of the C arm 15, and movement of the top plate 14. Furthermore, for example, the processing circuitry 21 controls the collimator control circuitry 20 according to an instruction of the operator, and adjusts the collimator of the collimator blades in the collimator 13, thereby controlling an irradiation range of an X-ray to be irradiated onto the subject P.

Moreover, the processing circuitry 21 controls image-data generation processing performed by the image-data generating circuitry 24, image processing or analysis processing performed by the image processing circuitry 26, and the like. Furthermore, the processing circuitry 21 controls to display a GUI to accept an instruction of the operator, an image stored in the storage circuitry 25, and the like on the display 23. Moreover, the processing circuitry 21 controls the injection timing of a contrast agent by transmitting a signal indicating start and end of the contrast agent injection to the injector 30. Furthermore, the processing circuitry 21 associates time information of an ECG received from the electrocardiograph 40 and time information of image data generated by the image-data generating circuitry 24. Details of the calculating function 211, the acquiring function 212, and the control function 213 by the processing circuitry 21 are described later. Moreover, the processing circuitry 21 is one example of a processing circuitry in claims.

As above, one example of the configuration of the X-ray diagnostic apparatus 100 has been explained. With such a configuration, the X-ray diagnostic apparatus 100 according to the present embodiment facilitates stereoscopic viewing of a dynamic part by the processing performed by the processing circuitry 21 explained in detail below. Acquisition and display of a stereoscopic image by the X-ray diagnostic apparatus 100 are explained herein. As described above, in the X-ray diagnostic apparatus 100, for example, the display 23 displays a stereoscopic image by emitting the right eye image and the left eye image to the right eye and the left eye of an observer, respectively. Specifically, the X-ray diagnostic apparatus 100 collects parallax images, the point of views of which are shifted by a predetermined angle relative to a subject part, to display on the display 23. For example, the X-ray diagnostic apparatus 100 acquires X-ray images, the points of view of which are shifted by "4°" relative to a subject part as a right eye image and a left eye image as two images of a right eye image and a left eye image, and displays them on the display 23. Here, the predetermined angle may be determined at any timing as long as it is before collecting the parallax images. For example, the predetermined angle may be determined in advance and preset. Also, the predetermined angle may be determined at the timing of setting the collection condition of X-ray image. Also, the predetermined angle may be determined at the timing just before collecting the parallax images.

When a subject part is a static part, the X-ray diagnostic apparatus 100 collects X-ray images, the points of view (collecting direction) are shifted by a predetermined angle relative to the subject part, by changing the angle of the C arm 15. As one example, the X-ray diagnostic apparatus 100 controls the C arm 15, and collects an X-ray image at each of a predetermined position and a position at which the C arm 15 is rotated from the predetermined position by "4°" to emit the images to the right eye and the left eye of the observer, respectively, thereby displaying a stereoscop image of the static part. Here, the predetermined position may be determined at any timing as long as it is before collecting the parallax images. For example, the predetermined position may be determined in advance and preset. Also, the predetermined position may be determined at the timing of setting the collection condition of X-ray image. Also, the predetermined position may be determined at the timing just before collecting the parallax images.

Figure 2:
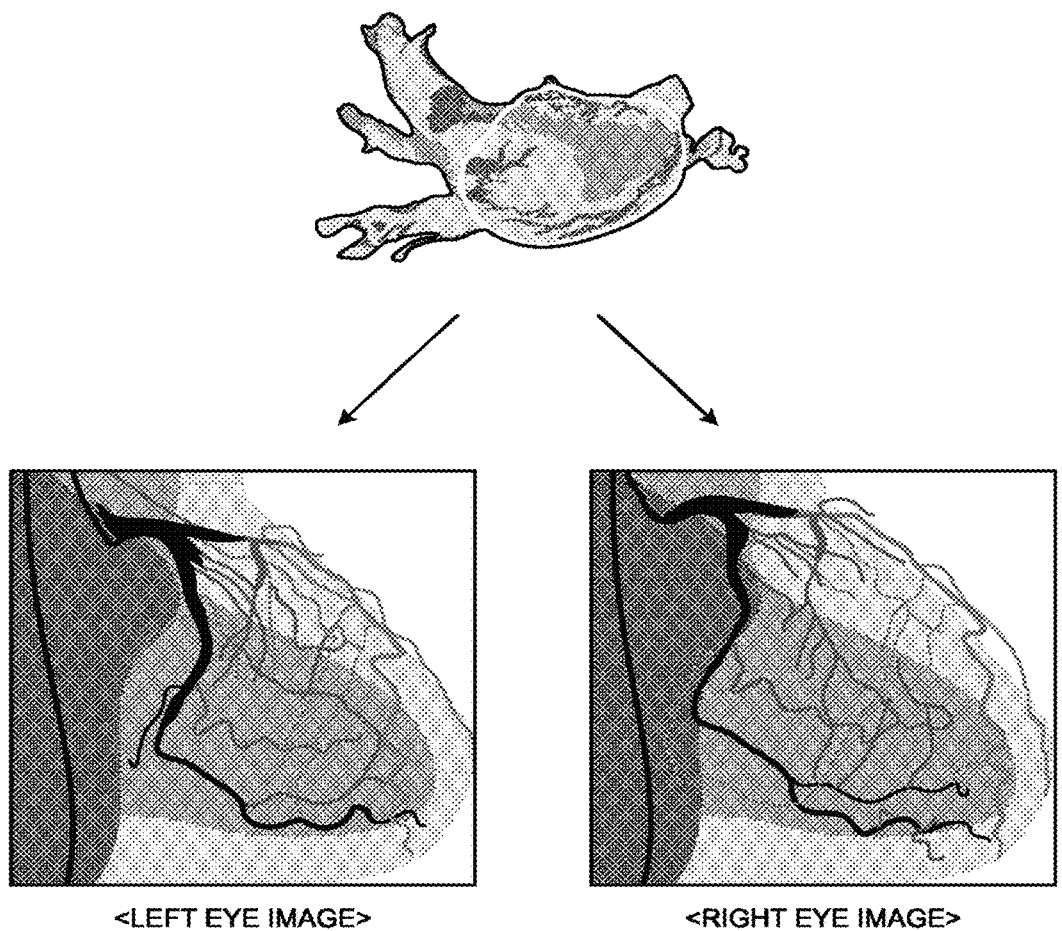
FIG. 2 shows one example of acquisition of parallax images of a dynamic part according to the first embodiment.

On the other hand, when the subject part is a dynamic part, even if X-ray images are collected changing the angle of the C arm 15, the subject part moves. Therefore, collection of parallax images, the points of view of which are shifted by a predetermined angle can be difficult. Therefore, the X-ray diagnostic apparatus 100 collects an X-ray image in a state in which the C arm 15 is fixed, and acquires multiple X-ray images in which the position of the subject part is changed by a predetermined angle, as parallax images. FIG. 2 shows one example of acquisition of parallax images of a dynamic part according to the first embodiment. For example, the X-ray diagnostic apparatus 100 acquires X-ray images that are drawn at positions at which a focused part moves by a predetermined angle, as a light eye image and a left eye image, respectively. That is, the X-ray diagnostic apparatus 100 acquires two pieces of X-ray images acquired when the focused part that moves with heartbeats is moved by a predetermined angle, as a right eye image and a left eye image.

When a heart is a subject part, for example, a guidewire inserted in a coronary artery, a stent set in a coronary artery, an aneurysm, a thrombus, a stenosis, a myocardium region, and the like are to be a region of interest (focused part). That is, when imaging a heart as a subject part, the X-ray diagnostic apparatus 100 acquires two X-ray images for which a moving distance of the region of interest that moves with the heart beat corresponds to the predetermined angle.

Specifically, the acquiring function 212 acquires medical images in which the moving distance of the focused part (region of interest) between the images corresponds to a distance derived from a parallax angle. More specifically, the acquiring function 212 acquires medical images in which the moving distance of the focused part (region of interest) matches with the distance derived from the parallax angle, or medical images in which the moving distance of the focused part (region of interest) is approximated to the distance derived from the parallax angle. That is, the acquiring function 212 acquires parallax images, the parallax of which is the predetermined angle, based on the moving distance of the region of interest. In the following, one example of acquisition of parallax images by the X-ray diagnostic apparatus 100 is explained using FIG. 3 to FIG. 6B. FIG. 3 to FIG. 6B show a case in which the subject part is a heart and the region of interest is a marker of a guidewire. FIG. 3 to FIG. 6B show acquisition of parallax images from among X-ray images (frame group) that are collected over time with the heart as a subject.

Figure 3:
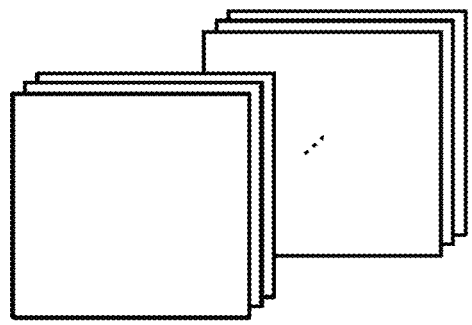
FIG. 3 is a diagram for explaining one example of a region of interest according to the first embodiment.
Figure 3:
Figure 3:
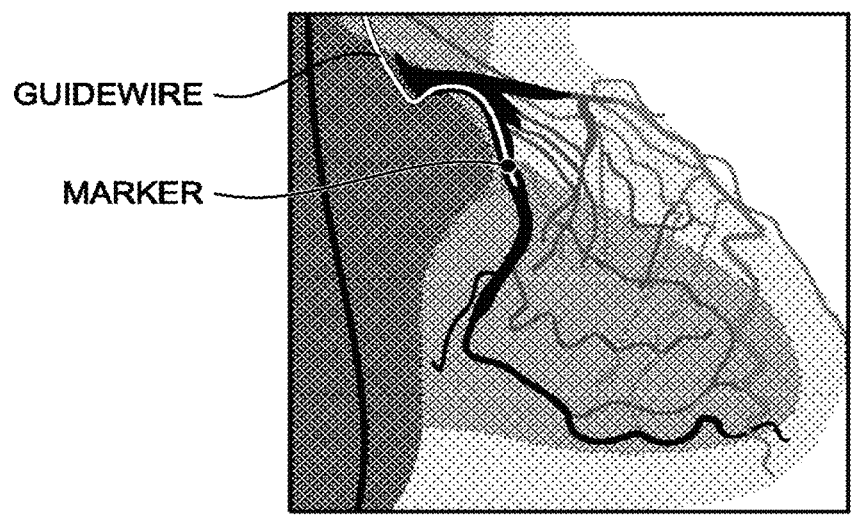

FIG. 3 is a diagram for explaining one example of a region of interest according to the first embodiment. For example, the acquiring function 212 acquires X-ray images (frames) in which a marker of a guidewire is drawn, from a frame group obtained by imaging the heart over time as shown in FIG. 3 as parallax image. The region of interest can be specified by an observer, or can be extracted automatically. For example, when it is specified by an observer, the control function 213 displays the frame group shown in FIG. 3 on the display 23 in chronological order. The input circuitry 22 then accepts a specification operation of the region of interest (for example, the marker of the guidewire) from an observer that is observing the frame group. When the input circuitry 22 accepts the specification operation of the region of interest, the calculating function 211 performs tracking processing for the region of interest for which the specification operation has been accepted, thereby extracting the region of interest (for example, the marker of the guidewire) included in each frame of the frame group.

The acquiring function 212 acquires parallax images from the frames from which the region of interest (for example, the marker of the guidewire) is extracted by the calculating function 211. Specifically, the acquiring function 212 acquires the parallax images based on the moving distance of the region of interest between the frames that is calculated by the calculating function 211. Calculation of the moving distance by the calculating function 211 is described in detail later. Because the observer tends to use a frame in which the region of interest is clearly drawn when specifying the region of interest, the acquiring function 212 can acquire, for example, the frame with which the specification operation of the region of interest is accepted, as one of the parallax images.

Moreover, when the region of interest is automatically extracted, the calculating function 211 extracts the region of interest (for example, the marker of the guidewire) included in each frame of the frame group, for example, by image processing such as pattern matching. The acquiring function 212 acquires parallax images from the frames from which the region of interest (for example, the marker of the guidewire) is extracted by the calculating function 211. Also when the region of interest is automatically extracted, the acquiring function 212 acquires parallax images based on the moving distance of the region of interest between the frames that is calculated by the calculating function 211. The acquiring function 212 can acquire, for example, a frame in which the region of interest is clearly drawn from among frames in which the region of interest is extracted, as one of the parallax images.

For the parallax images acquired by the acquiring function 212, based on the position of the region of interest in one frame and the position of the region of interest in the other frame, a right eye image or a left eye image is determined for each image. For example, the frame shown in FIG. 3 is acquired as one of the parallax images, and when the position of the marker is on a right side relative to the position of the marker in the other frame of the parallax images, the frame shown in FIG. 3 is to be a left eye image. On the other hand, when the position of the marker in FIG. 3 is on a left side relative to the position of the marker of the other frame of the parallax images, the image shown in FIG. 3 is to be a right eye image.

As described above, when the region of interest is extracted from each frame in the frame group, the acquiring function 212 acquires frames in which the moving distance of the region of interest between the frames corresponds to the distance that is derived from the parallax angle of the region of interest. The calculating function 211 calculates the distance between positions of the region of interest in the respective frames for the acquiring function 212 to acquire parallax images. For example, the calculating function 211 calculates a distance between a position of the marker of the guidewire in a frame acquired in FIG. 3, and a position of the marker of the guidewire in another frame. The acquiring function 212 acquires frames of parallax images based on the distance calculated by the calculating function 211. When a frame with which the specification operation for the region of interest is acquired as one of the parallax images, or when a frame in which the region of interest is clearly drawn is acquired as one of the parallax images, the acquiring function 212 acquires the other frame of the parallax images based on the distance calculated by the calculating function 211.

Figure 4:
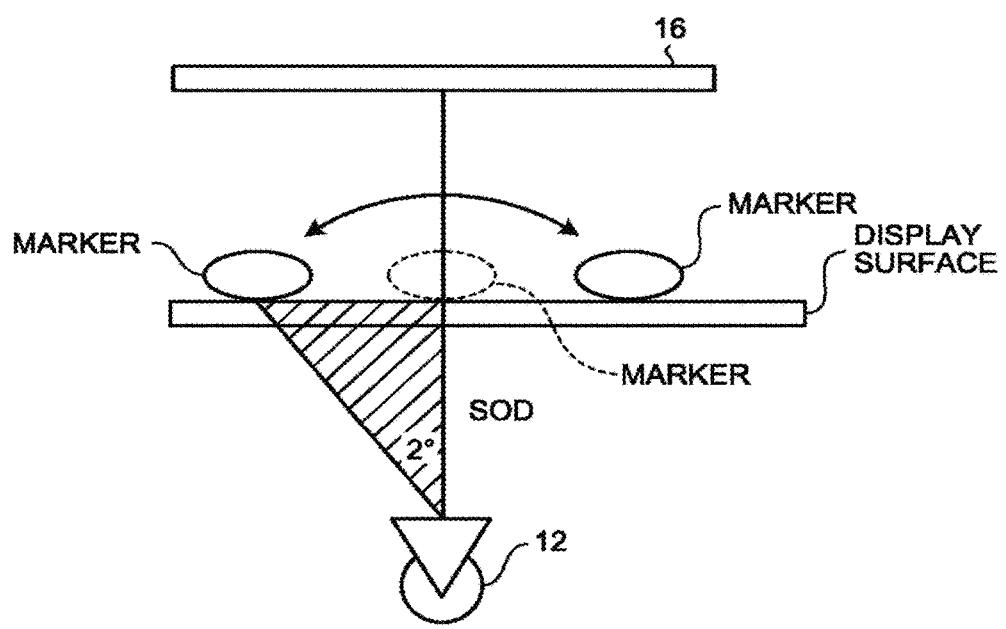
FIG. 4 is a diagram for explaining a parallax angle and a distance of a region of interest according to the first embodiment.

The distance derived from a parallax angle is explained using FIG. 4. FIG. 4 is a diagram for explaining a parallax angle and a distance between positions of a region of interest according to the first embodiment. FIG. 4 shows an example in which a marker of a guidewire is used as a region of interest. For example, as shown in FIG. 4, when the marker moves alternately right and left (horizontal direction) with heart beats, an angle formed between a line connecting a position of the marker positioned on the left side relative to an image center (center line of a display surface) and the X-ray tube 12, and a line connecting a position of the marker positioned on the right side relative to the image center (center line on the display surface) and the X-ray tube 12 is the parallax angle. The distance derived from the parallax angle indicates the distance between the marker on the right side and the marker on the left side relative to the image center when the parallax angle is a predetermined angle.

For example, when the parallax angle is "4°", as shown in FIG. 4, based on the angle formed between a line connecting the X-ray tube 12 and the marker on the left side and a line connecting the X-ray tube 12 and the image center being "2°", the distance between the image center and the marker is calculated. Thus, a frame in which the marker is drawn at the position corresponding to the calculated distance is acquired as one of the parallax images. That is, a frame in which the marker is drawn at a position corresponding to the calculated distance on the left side relative to the image center is acquired as a right eye image. Moreover, a frame in which the marker is drawn at a position corresponding to the calculated distance on the right side relative to the image center is acquired as a left eye image. Details of calculation of the distance are described later.

Figure 5:
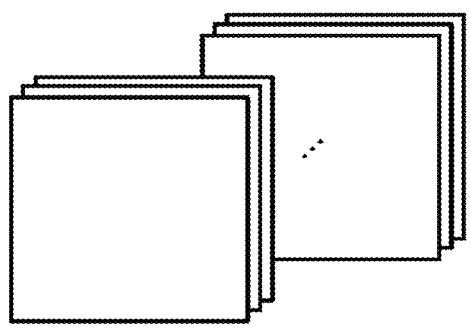
FIG. 5 shows parallax images according to the first embodiment.
Figure 5:
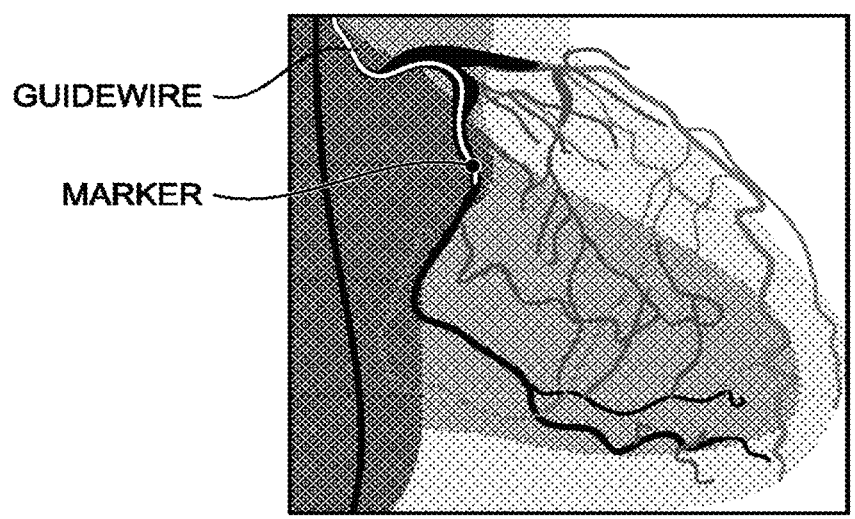

When the distance is thus calculated by the calculating function 211, the acquiring function 212 acquires parallax images based on the calculated distance. That is, the acquiring function 212 acquires a frame in which the marker of the region of interest is moved by the distance derived from the parallax angle. For example, the acquiring function 212 acquires the left eye image shown in FIG. 3 and the right eye image shown in FIG. 5. FIG. 5 shows a parallax image.

Figure 6A:
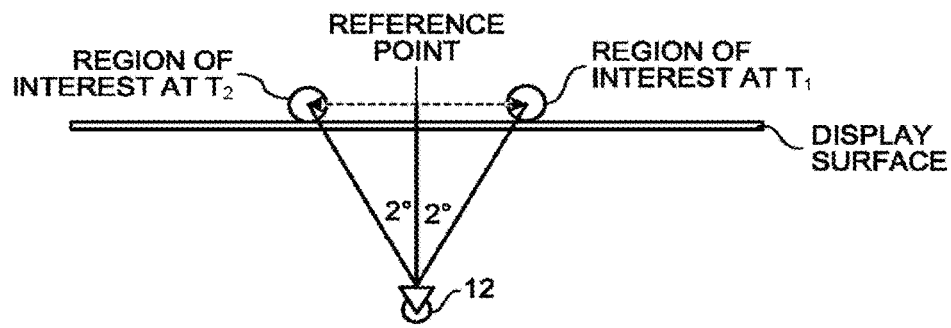
FIG. 6A is a diagram for explaining a calculation example of a moving distance according to the first embodiment.
Figure 6B:
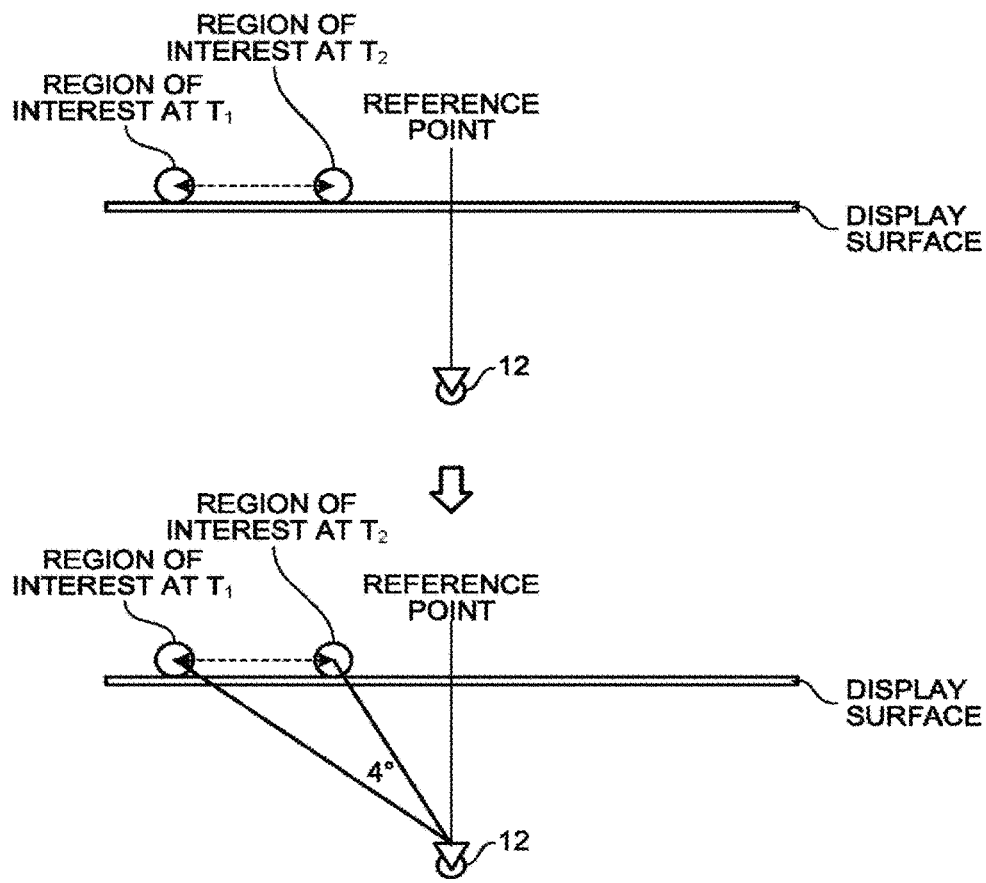
FIG. 6B is a diagram for explaining a calculation example of a moving distance according to the first embodiment.

As described, the acquiring function 212 acquires parallax images based on the moving distance calculated by the calculating function 211. The calculation of the moving distance by the calculating function 211 varies according to a position to which a region of interest moves. Specifically, it differs between cases when the region of interest passes across the image center and when the region of interest does not pass across the image center. The calculation of each case is explained below using FIG. 6A and FIG. 6B. FIG. 6A and FIG. 6B are diagrams for explaining a calculation example of a moving distance according to the first embodiment. FIG. 6A shows the case in which a region of interest passes across the image center. Moreover, FIG. 6B shows the case in which a region of interest does not pass across the image center. FIG. 6A and FIG. 6B show a case in which the parallax angle is "4°".

First, the case in which a region of interest passes across the image center is explained. As shown in FIG. 4 also, when a region of interest passes across the image center (that is, when the region of interest moves between two regions that are divided by the image center), the calculating function 211 calculates the distance based on a triangle formed by the X-ray tube 12, the image center (reference point), and the region of interest (for example, a marker) positioned on the right side (or the left side) of the image center as shown in FIG. 6A. That is, the calculating function 211 calculates the distance between the reference point and the region of interest on the right side based on the angle formed between a line connecting the X-ray tube 12 and the position of the region of interest on the right side, and a line connecting the X-ray tube 12 and the reference point being "2°". The distance (SOD) between the region of interest on the image center (reference point) and the X-ray tube 12 can be acquired from the imaging condition. Therefore, the calculating function 211 calculates, for example, a "distance between the reference point and the region of interest on the right side" by "SOD×tan 2°". As one example, when "SOD=70 cm", the calculating function 211 calculates as "the distance between the reference point and the region of interest=2.4 cm".

That is, the acquiring function 212 acquires a frame of a point of time (for example, at $T_1$) when the region of interest has moved rightward by "2.4 cm" from the image center (reference point) as a left eye image. Similarly, the acquiring function 212 acquires a frame of a point of time (for example, at $T_2$) when the region of interest has moved leftward by "2.4 cm" from the image center (reference point) as a right eye image.

Next, the case in which the region of interest does not pass across the image center is explained. The case in which the region of interest does not pass across the image center is a case in which the region of interest moves within either one of two regions that are divided by the image center, and it is, for example, a case in which the region of interest moves only in a region on the left side of the image center as shown in a drawing on an upper side of FIG. 6B. In such a case, the calculating function 211 calculates a distance based on a triangle formed by the X-ray tube 12 and the respective regions of interest. That is, the calculating function 211 calculates a moving distance of the region of interest with which an angle formed between a line connecting the X-ray tube 12 and one of the regions of interest and line connecting the X-ray tube 12 and the other one of the regions of interest is "4°".

As one example, the calculating function 211 assumes a frame as one frame of the parallax images, and calculates a moving distance according to the parallax angle based on the position of a region of interest in the assumed frame. For example, the calculating function 211 assumes a frame at $T_1$ as one frame of the parallax images, and calculates the distance according to the angle "4°" of a parallax. That is, the calculating function 211 calculates a distance between the region of interest at $T_1$ and the reference point shown in FIG. 6B. The calculating function 211 then calculates an angle "θ" that is formed between a line connecting the region of interest at $T_1$ and the X-ray tube 12 and a line connecting the reference point and the X-ray tube 12, from the calculated distance and "SOD". Furthermore, the calculating function 211 calculates a distance between the reference point and the region of interest at an angle "θ−4" obtained by subtracting the parallax angle from the calculated angle "θ".

The acquiring function 212 acquires a frame at the time (for example, $T_2$) when the region of interest has moved leftward from the image center (reference point) by the calculated distance as another frame of the parallax images. That is, the acquiring function 212 acquires the frame at $T_1$ as a left eye image, and the frame at $T_2$ as a right eye image.

As described above, the calculating function 211 calculates moving distances by different methods when a region of interest passes across the image center and when the region of difference does not pass across the image center, respectively. The acquiring function 212 acquires each frame of the parallax images based on the moving distance calculated by the calculating function 211. The parallax angle can be set arbitrarily by an observer. That is, the calculating function 211 calculates a moving distance according to the parallax angle set by the observer, and the acquiring function 212 acquires a frame corresponding to the calculated moving distance as a parallax image.

Moreover, the acquiring function 212 acquires two frames in which the moving distance of the region of interest corresponds to the distance calculated by the calculating function 211 as the parallax images, but the moving distance of the region of interest is not required to match with the calculated distance. That is, the acquiring function 212 can acquires two frames in which the moving distance of the region of interest is approximated to the calculated distance as parallax images. For example, when there are no frames in which the moving distance matches with the calculated distance, the acquiring function 212 acquires two frames in which the moving distance of the region of interest is closest to the calculated distance as parallax images.

Furthermore, the distance described above can be converted into the number of pixels. In such a case, for example, the calculating function 211 converts the calculated distance into the number of pixels of the display 23. The acquiring function 212 acquires parallax images based on the number of pixels obtained by conversion.

The control function 213 causes the display 23 that displays a stereoscopic image to display the parallax images acquired by the acquiring function 212. The control function 213 can display the parallax images on the display 23 after rotating a moving direction of a region of interest to be in a horizontal direction. For example, the moving direction of the region of interest that moves with movement of a dynamic part is not necessarily the horizontal direction. Therefore, the control function 213 rotates the parallax images such that the moving direction of the region of interest to be the horizontal direction (to be parallel to both eyes of the observer).

Figure 7:
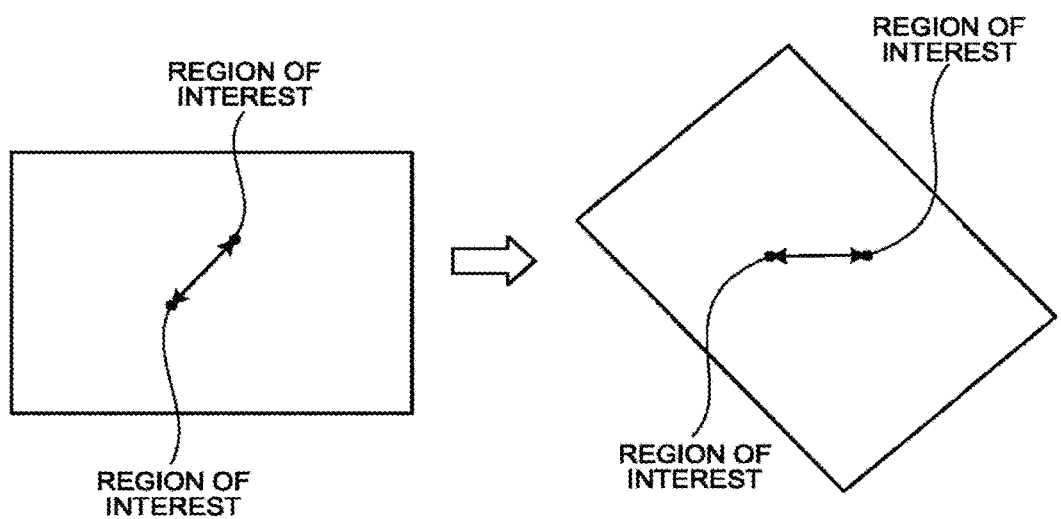
FIG. 7 shows one example of rotation of parallax images according to the first embodiment.

FIG. 7 shows one example of rotation of parallax images according to the first embodiment. For example, as shown in the drawing on the left side of FIG. 7, when a region of interest is moving in an oblique direction, the control function 213 rotates the parallax image such that the moving direction of the region of interest is the horizontal direction. That is, the control function 213 rotates the parallax image such that the moving direction of the region of interest is the horizontal direction by rotating each of the right eye image and the left eye image.

Figure 8:
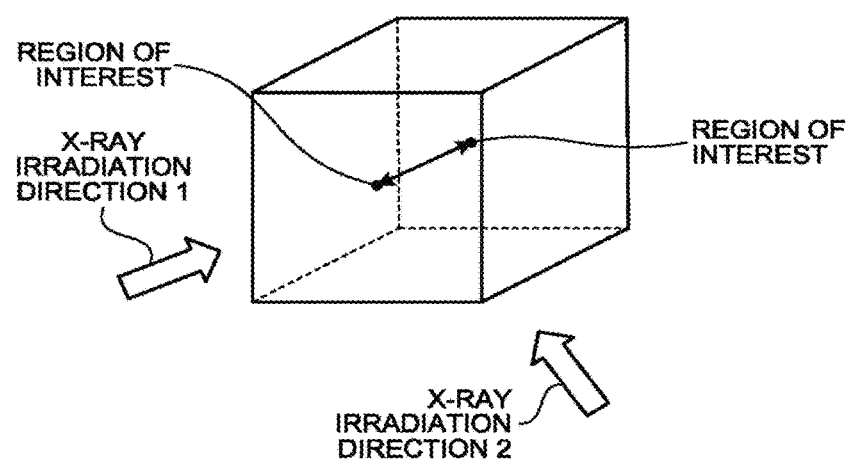
FIG. 8 is a diagram for explaining one example of control of an irradiation direction of an X-ray by a control function according to the first embodiment.

Moreover, the control function 213 can control an irradiation direction of an X-ray such that the region of interest moves in a frame group. FIG. 8 is a diagram for explaining one example of control of an irradiation direction of an X-ray by the control function 213 according to the first embodiment. FIG. 8 shows a three-dimensional moving direction of a region of interest in a subject body. For example, when an X-ray is irradiated from an X-ray irradiation direction 1 in a state in which the region of interest is moving as shown in FIG. 8, the region of interest moves in a depth direction of an X-ray image. In this case, the position of the region of interest in the frame group changes little, and it is difficult to acquire parallax images. Therefore, the control function 213 controls, for example, the C arm 15 such that the irradiation direction of an X-ray is an X-ray irradiation direction 2 shown in FIG. 8. Thus, the position of the region of interest is to vary among frames, and it becomes possible to acquire parallax image.

The irradiation direction of an X-ray can be controlled such that the moving direction of the region of interest is the horizontal direction, or can be controlled such that the position of the region of interest just varies among frames. When it is controlled such that the position of the region of interest varies among frames, the control function 213 rotates the right eye image and the left eye image such that the moving direction of the region of interest is the horizontal direction.

Figure 9:
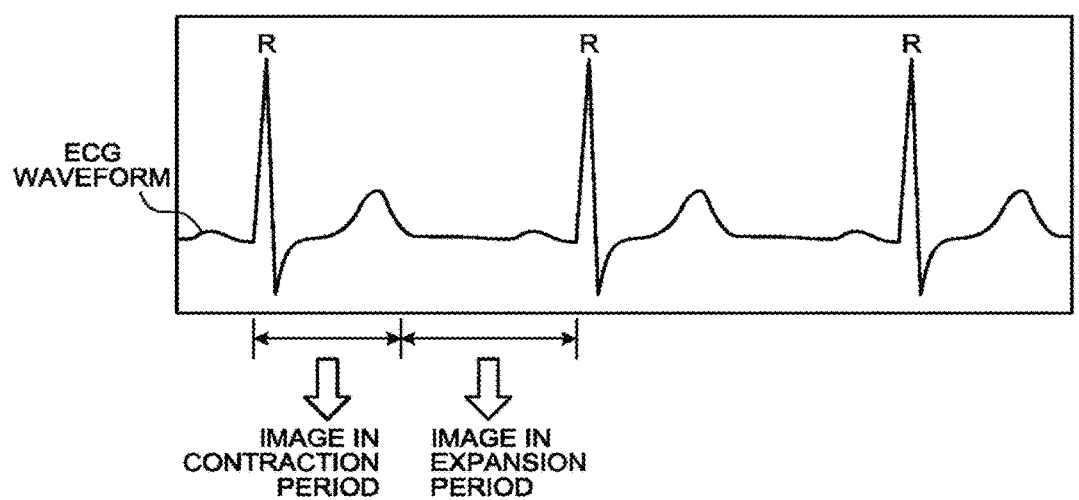
FIG. 9 is a diagram for explaining one example of acquisition of parallax images by using phase information according to the first embodiment.

In the embodiment described above, the case in which a right eye image and a left eye image are acquired from a frame group has been explained. However, embodiments are not limited thereto, and for example, a case in which parallax images are acquired by using a phase can be included. Specifically, for medical images of a part moving periodically, the acquiring function 212 acquires a medical image at a phase in which a moving distance of a region of interest between images corresponds to a distance that is derived from a parallax angle. FIG. 9 is a diagram for explaining one example of acquisition of parallax images by using phase information according to the first embodiment. For example, the acquiring function 212 acquires an image in a contraction period and an image in an expansion period as parallax images, based on an ECG waveform that is acquired from a subject in parallel with imaging of an X-ray image as shown in FIG. 9.

In such a case, for example, the control function 213 associates frames that are acquired at the time of fluoroscopy before imaging, with phases at the time of acquisition, respectively. The acquiring function 212 acquires parallax images from the frames acquired by fluoroscopy as described above, and acquires a phase of each frame of the acquired parallax images. When imaging is started after fluoroscopy, the acquiring function 212 acquires two frames that correspond to the acquired phases.

The control function 213 can cause the display 23 to display the parallax images described above by various methods. For example, the control function 213 causes the display 23 to display the entire parallax images. Moreover, for example, the control function 213 causes the display 23 to display a region that is a part of a region of a medical image and that includes a region of interest. FIG. 10A shows a display example of parallax images by the control function 213 according to the first embodiment. For example, the control function 213 causes the display 23 to display a left eye image and a right eye image that show only a region including a marker of a guidewire, which is the region of interest, as shown in FIG. 10A. For example, in a medical image of a heart, it is seldom the case that the entire region of the image moves in the identical direction. Therefore, it is difficult to observe the entire region of the image as one stereoscopic image, and accordingly, the control function 213 controls to display only the region including the region of interest. A region other than the region is controlled not to be displayed, for example, by arranging a shielding object such as an electronic shutter. Moreover, for a region other than the region, it can also be arranged such that a corresponding region in either one of the right eye image and the left eye image is displayed.

Figure 10B:
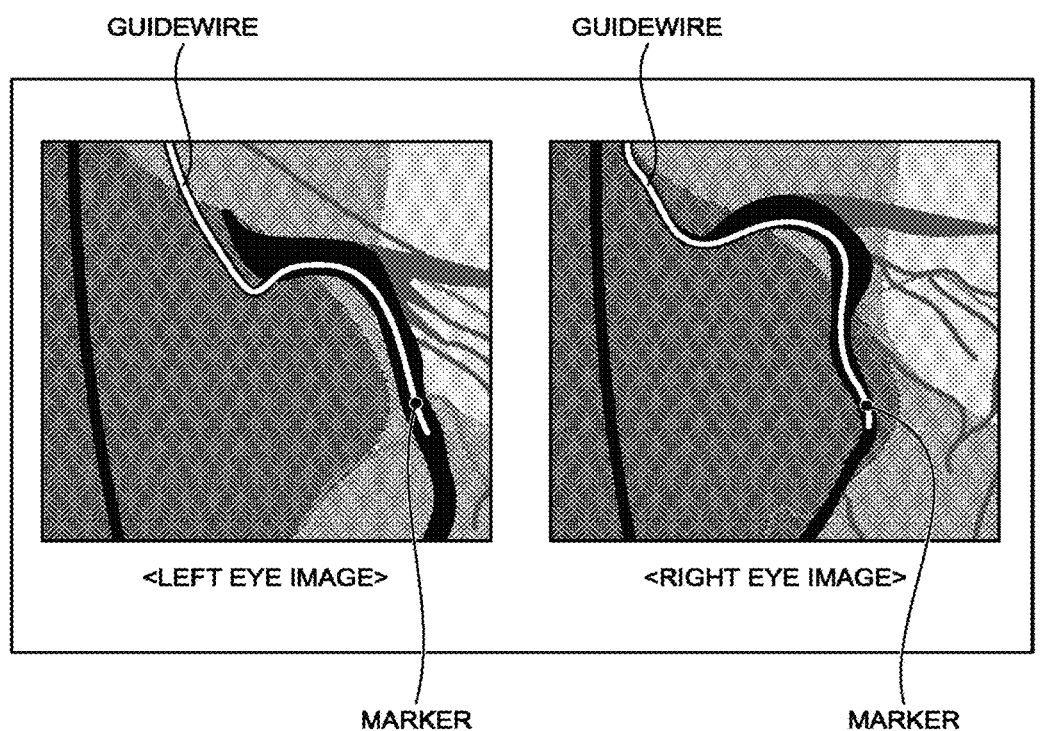
FIG. 10B shows a display example of parallax images by the control function according to the first embodiment.

Furthermore, the control function 213 can display the region including a region of interest in an enlarged manner on the display 23. FIG. 10B shows a display example of parallax images by the control function according to the first embodiment. For example, for the left eye image and the right eye image, the control function 213 causes to display respective images in which the region including a marker of a guidewire, which is the region of interest, is enlarged as shown in FIG. 10B, as parallax images.

Next, processing performed by the X-ray diagnostic apparatus 100 according to the first embodiment is explained using FIG. 11 and FIG. 12. The X-ray diagnostic apparatus 100 according to the first embodiment can perform processing for an X-ray image that is collected as described above (processing in post process), and processing for an X-ray image that is collected in real time (processing at Live). The processing is explained below sequentially.

FIG. 11 is a flowchart showing a processing procedure of a post process according to the first embodiment. Steps S101, S102, S106, S107, and S108 are steps performed by the processing circuitry 21 by reading a program that corresponds to the control function 213 from the storage circuitry 25. Moreover, steps S103 and S105 are steps performed by the processing circuitry by reading a program that corresponds to the acquiring function 212 from the storage circuitry 25. Furthermore, steps S104 and S105 are steps performed by the processing circuitry 21 by reading a program that corresponds to the calculating function 211 from the storage circuitry 25. At step S101 and step S102, the processing circuitry 21 displays a collected X-ray image on the display 23, and determines whether it is in the phase mode to acquire parallax images based on a phase.

When it is in the phase mode (step S102: YES), the processing circuitry 21 acquires a phase image corresponding to a parallax image based on phase information stored, associated in advance at step S103. On the other hand, when it is not in the phase mode (step S102: NO), the processing circuitry 21 identifies a region of interest in each image at step S104. Subsequently, at step S105, the processing circuitry 21 calculates a moving amount of the region of interest between images, and acquires two images forming a parallax angle as parallax images.

At step S106, the processing circuitry 21 determines whether a moving direction of the region of interest in the acquired images is horizontal. When the moving direction of the region of interest is not horizontal (step S106: NO), the processing circuitry 21 rotates the images so that the region of interest moves horizontally at step S107, and displays a stereoscopic image at step S108. On the other hand, when the moving direction of the region of interest is horizontal (step S106: YES), the processing circuitry 21 displays a stereoscopic image at step S108.

FIG. 12 is a flowchart showing a processing procedure at the time of Live according to the first embodiment. Steps S201, S203, S204, S206, S207, S206, and S209 shown in FIG. 12 are steps performed by the processing circuitry 21 by reading the program that corresponds to the control function 213 from the storage circuitry 25. Moreover, steps S202 and S205 shown in FIG. 12 are steps performed by the processing circuitry 21 by reading the program that corresponds to the calculating function 211 from the storage circuitry 25. Furthermore, step S205 shown in FIG. 12 is a step performed by the processing circuitry 21 by reading the program that corresponds to the acquiring function 212 from the storage circuitry 25. At step S201, the processing circuitry 21 displays a Live fluoroscopic image.

At step S202 and step S203, the processing circuitry 21 identifies a region of interest per image, and determines whether the region of interest moves in parallel in the images. When the region of interest does not move in parallel, (step S203: NO), the processing circuitry 21 controls the irradiation direction of an X-ray such that the region of interest moves in parallel in the images at step S204, and calculates a moving amount of the region of interest between images and acquires two parallax images forming a parallax angle at step S205.

On the other hand, when the region of interest moves in parallel (step S203: YES), the processing circuitry 21 calculates a moving amount of the region of interest between images at step S205, and acquires two parallax images forming the parallax angle at step S205. Thereafter, at step S206, the processing circuitry 21 stores phase information of the acquired images in the storage circuitry 25. The processing circuitry 21 then starts fluoroscopy or imaging of an X-ray image. Furthermore, the processing circuitry 21 acquires X-ray images of the times corresponding to the phase information stored in the storage circuitry 25 as parallax images.

At step S207, the processing circuitry 21 determines whether a moving direction of the region of interest in the acquired images is horizontal. When the moving direction of the region of interest is not horizontal (step S207: NO), the processing circuitry 21 rotates the images so that that region of interest moves horizontally at step S208, and displays a stereoscopic image at step S209. On the other hand, when the moving direction of the region of interest is horizontal (step S207: YES), the processing circuitry 21 displays a stereoscopic image at step S209.

As described above, according to the first embodiment, the acquiring function 212 acquires plural medical images in which a moving distance of a region of interest (focused part) between images corresponds to a distance that is derived from a parallax angle. The control function 213 displays the medical images on the display 23 that displays a stereoscopic image. Therefore, the X-ray diagnostic apparatus 100 according to the first embodiment enables to have a stereoscopic view of a dynamic part easily.

Moreover, according to the first embodiment, the acquiring function 212 acquires plural medical images in which a moving distance of a region of interest matches with a distance that is derived from a parallax angle, or plural medical images in which a moving distance of a region of interest is approximated to a distance that is derived from a parallax angle. Therefore, the X-ray diagnostic apparatus 100 according to the first embodiment enables to acquire optimal parallax images according to a situation.

Furthermore, according to the first embodiment, the calculating function 211 derives distance corresponding to a parallax angle when a region of interest moves between two regions that are divided by an image center, and the acquiring function 212 acquires two medical images in which a distance of the region of interest between images corresponds to the derived distance. Moreover, the calculating function 211 derives a distance corresponding to a parallax angle when a region of interest moves within either one of two regions that are divided by an image center. The acquiring function 212 acquires two medical images in which a distance between positions of the region of interest in the respective images corresponds to the derived distance. Subsequently, the control function 213 displays the two medical images on the display 23. Therefore, the X-ray diagnostic apparatus 100 according to the first embodiment enables to acquire optimal parallax images according to a position to which a region of interest moves.

Moreover, according to the first embodiment, the control function 213 displays plural medical images after rotating the medical images so that the moving direction of a region of interest is the horizontal direction. Therefore, the X-ray diagnostic apparatus 100 according to the first embodiment enables to display a stereoscopic image no matter how a region of interest moves in images.

Furthermore, according to the first embodiment, the control function 213 controls an irradiation direction of an X-ray such that a moving distance of a region of interest between images corresponds to a distance that is derived from a parallax angle. Therefore, the X-ray diagnostic apparatus 100 according to the first embodiment enables to acquire parallax images to show a region of interest in a stereoscopic view no matter which direction the region of interest is moving in a subject body.

Moreover, according to the first embodiment, for medical images of a part that moves periodically, the acquiring function 212 acquires medical images at phases in which a moving distance of a region of interest between images corresponds to a distance derived from a parallax angle. Therefore, the X-ray diagnostic apparatus 100 according to the first embodiment enables to acquire parallax images easily.

Furthermore, according to the first embodiment, the control function 213 displays an region that is a part of a medical image and that includes a region of interest on the display 23. Moreover, the control function 213 causes the display 23 to display the region in an enlarged manner. Therefore, the X-ray diagnostic apparatus 100 according to the first embodiment enables to display a stereoscopic image with which observation of a region of interest is facilitated.

Second Embodiment

The first embodiment has been explained, but various different embodiments other than the first embodiment described above can be implemented.

In the embodiment described above, a case of acquiring two frames as parallax images is explained as an example. However, embodiments are not limited thereto. For example, a case of acquiring three or more frames as parallax images can be included. In such a case, for example, the acquiring function 212 acquires three or more frames in which a moving distance of a region of interest among frames corresponds to a distance calculated by the calculating function 211. The control function 213 uses, for example, a beam controller such as a lenticular lens, and thereby causes the display 23 that can display a stereoscopic view of parallax images including three or more frames to display the acquired three or more frames.

Moreover, in the embodiment described above, a case in which two frames are acquired from a frame group collected over time, and a still image of a stereoscopic image is displayed is explained. However, embodiments are not limited thereto. For example, a case in which a moving image of a stereoscopic image is displayed by acquiring and displaying plural parallax images from a frame group collected over time can be included. For example, a moving image of guidewire being inserted into a blood vessel can be displayed stereoscopically. In such a case, the calculating function 211 and the acquiring function 212 perform the processing described above for a frame group at points of time when movement of the guidewire is small, and the acquiring function 212 thereby acquires parallax images at each of the points of time. Subsequently, the control function 213 sequentially displays the acquired parallax images in chronological order.

Furthermore, the respective components of the respective devices illustrated in the first embodiments are of functional concept, and it is not necessarily required to be configured physically as illustrated. That is, specific forms of distribution and integration of the respective devices are not limited to the ones illustrated, and all or a part thereof can be configured to be distributed or integrated functionally or physically in arbitrary units according to various kinds of load, usage conditions, and the like. Furthermore, as for the respective processing functions performed by the respective devices, all or an arbitrary part thereof can be implemented by a CPU and a computer program that is analyzed and executed by the CPU, or can be implemented as hardware by wired logic.

Moreover, the display method explained in the above embodiments can be implemented by executing a control program prepared in advance by a computer, such as a personal computer and a workstation. The display program can be distributed through a network such as the Internet. Furthermore, the control program can be stored in a computer-readable recording medium, such as a hard disk, a flexible disk (FD), a compact-disc read-only memory (CD-ROM), a magneto optical disk (MO), and a digital versatile disc (DVD) and can be executed by being read by a computer from the recording medium.

As explained above, according to at least one of the embodiments, it is possible to have a stereoscopic view of a dynamic part easily.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising:
processing circuitry configured to
acquire a plurality of medical images, each including a region of interest, in chronological order,
identify two medical images among the plurality of medical images, a moving distance of the region of interest between the two medical images corresponding to a distance derived from a parallax angle, and
cause a display to display a stereoscopic image by displaying the identified two medical images.

2. The X-ray diagnostic apparatus according to claim 1, wherein
the processing circuitry is configured to identify two medical images in which the moving distance of the region of interest matches with the distance derived from the parallax angle, or is approximated to the distance derived from the parallax angle.

3. The X-ray diagnostic apparatus according to claim 1, wherein
the processing circuitry is configured to derive the distance corresponding to the parallax angle when the region of interest moves between two regions that are divided by an image center line of one of the acquired medical images, identify two medical images in which a distance between positions of the region of interest in images corresponds to the derived distance, and cause the display to display a stereoscopic image by displaying the identified two medical images.

4. The X-ray diagnostic apparatus according to claim 1, wherein
the processing circuitry is configured to derive the distance corresponding to the parallax angle when the region of interest moves within either one of two regions that are divided by an image center line of one of the acquired medical images, identify two medical images in which a distance between positions of the region of interest in images corresponds to the derived distance, and cause the display to display a stereoscopic image by displaying the identified two medical images.

5. The X-ray diagnostic apparatus according to claim 1, wherein
the processing circuitry is configured to cause the display to display a stereoscopic image by displaying the identified two medical images after rotating the medical images such that a moving direction of the region of interest is a horizontal direction.

6. The X-ray diagnostic apparatus according to claim 1, wherein
the processing circuitry is configured to control an irradiation direction of an X-ray such that the moving distance of the region of interest between images corresponds to the distance that is derived from the parallax angle.

7. The X-ray diagnostic apparatus according to claim 1, wherein
for medical images of a part that moves periodically, the processing circuitry is configured to identify each of medical images of two phases in which the moving distance of the region of interest between images corresponds to the distance that is derived from the parallax angle.

8. The X-ray diagnostic apparatus according to claim 1, wherein
the processing circuitry is configured to cause the display to display a region that is a part of the medical image, and that includes the region of interest.

9. The X-ray diagnostic apparatus according to claim 8, wherein
the processing circuitry is configured to cause the display to display the region in an enlarged manner.

10. An medical image displaying method comprising:
acquiring a plurality of medical images each including a region of interest in chronological order,
identifying two medical images among the plurality of medical images, a moving distance of the region of interest between the two medical images corresponding to a distance derived from a parallax angle, and
causing a display to display a stereoscopic image by displaying the identified two medical images.

* * * * *